(12) United States Patent
Toida

(10) Patent No.: US 6,636,755 B2
(45) Date of Patent: Oct. 21, 2003

(54) METHOD AND APPARATUS FOR OBTAINING AN OPTICAL TOMOGRAPHIC IMAGE OF A SENTINEL LYMPH NODE

(75) Inventor: Masahiro Toida, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 27 days.

(21) Appl. No.: 09/962,195

(22) Filed: Sep. 26, 2001

(65) Prior Publication Data

US 2002/0037252 A1 Mar. 28, 2002

(30) Foreign Application Priority Data

Sep. 26, 2000 (JP) ........................................ 2000/292105

(51) Int. Cl.[7] ................................................. A61B 5/05
(52) U.S. Cl. .......................... 600/407; 600/436; 600/475
(58) Field of Search .................................. 600/431, 436, 600/473, 476, 160, 475, 407; 356/345, 450, 456; 424/9.6; 250/458.1, 459.1

(56) References Cited

U.S. PATENT DOCUMENTS

| | | | | |
|---|---|---|---|---|
| 6,002,480 A | * | 12/1999 | Izatt et al. | 345/345 |
| 6,134,003 A | * | 10/2000 | Tearney et al. | 356/345 |
| 6,167,297 A | * | 12/2000 | Benaron | 600/431 |
| 6,350,431 B1 | * | 2/2002 | Snow et al. | 424/9.6 |

FOREIGN PATENT DOCUMENTS

JP    2000-124600    4/2000    ............ H05K/3/34

OTHER PUBLICATIONS

Houston, J. P. et al., "Sensitivity and depth penetration of continuous wave versus frequency–domain photon migration near–infrared fluorescence contrast enhanced imaging" Apr. 2003, Photochemistry and Photobiology; Augusta.*
Abstract JP2000–124600, Apr. 28, 2000.

* cited by examiner

Primary Examiner—Shawna J. Shaw
(74) Attorney, Agent, or Firm—Sughrue Mion, PLLC

(57) ABSTRACT

An apparatus for obtaining a cellular image to be used in performing a test for pathology of the sentinel lymph node, which is the first lymph node a cancer metastasizes to. The gamma radiation emitted from a near-infrared fluorescent colorant injected in advance into the vicinity of a tumor is detected by use of a gamma-probe. A fiber coupler separates the low-coherence light emitted from the light source of an OCT portion (Optical Coherence Tomography) into a signal-light to be projected onto the sentinel lymph node and a reference-light whose wavelength is slightly shifted. The signal-light is projected onto the sentinel lymph node, and interference is caused between the signal-light reflected from a predetermined depth within the sentinel lymph node and the reference-light. A balance differential detector measures the intensity of the interference-light, and a cellular level ultra high-resolution optical tomographic image of the sentinel lymph node is obtained.

12 Claims, 4 Drawing Sheets

METHOD AND APPARATUS FOR OBTAINING AN OPTICAL TOMOGRAPHIC IMAGE OF A SENTINEL LYMPH NODE

BACKGROUND OF THE INVENTION

1. Field of the Invention

The present invention relates in general to a method and apparatus for obtaining an optical tomographic image of a sentinel lymph node, and in particular, to detecting the sentinel lymph node, into which tumor cells first enter the lymph system from the primary nidus of a tumor, and obtaining an optical tomographic image of the sentinel lymph node.

2. Description of the Related Art

Recent years have seen increased rates in the early detection of cancer and the like, and cancerous and other diseased tissues are frequently surgically removed in the early stages of a disease. Generally, the objective of early surgical removal of cancerous tissue is the complete arresting of the disease, and frequently, in addition to the diseased tissue, a plurality of lymph nodes in the area surrounding the diseased tissue, from which there is a suspected danger of metastasis of the disease, are also removed. In addition, a test for pathology is performed on the excised lymph nodes to confirm whether or not the disease has metastasized thereto, and the course of post-surgical treatment is determined.

Due to the fact that it is not known whether or not the disease has metastasized to the lymph nodes during the performance of the surgical removal thereof, a plurality of lymph nodes in the surrounding vicinity of the diseased tissue is removed, and the burden on the patient is therefore great. Further, in the early stages of breast cancer, for example, the rate of metastasis of the disease to lymph nodes is 20 percent; for the 80 percent of the patients in whom the disease has not metastasized to the lymph nodes, the removal thereof is unnecessary.

In recent years, both the complete halting of the disease through surgical removal of the cancerous tissue and the preservation of the QOL (Quality of Life) of the patient are sought. To this end, one surgical method that has received much attention, which is aimed at preventing unnecessary removal of lymph nodes, is sentinel node navigation surgery. Hereinafter, a simple explanation of sentinel node navigation surgery will be given.

For cases in which cancer has metastasized to lymph nodes, it has become clear, in light of recent research, that it does not metastasize randomly, but is metastasize through the lymph system to the lymph nodes according to a set pattern. The first lymph node into which cancer cells enter from the primary nidus of a cancer is called a sentinel lymph node; it is held that for cases in which cancer has metastasized to the lymph nodes, the cancer has definitely metastasized to a sentinel lymph node.

Accordingly, by finding and excising the sentinel lymph node in a cancer removal surgery performed in the early stages of the disease, and preparing a sample of the excised sentinel lymph node and expediently performing a test for pathology thereon, it can be determined whether or not the cancer has metastasized to the lymph nodes.

For cases in which the cancer is determined not to have metastasized to the lymph nodes, it is unnecessary to remove the remaining lymph nodes. For cases in which the cancer is found to have metastasized to the lymph nodes, depending upon the conditions, a plurality of lymph nodes are surgically removed from the vicinity surrounding the diseased tissue.

By performing sentinel node navigation surgery, it becomes unnecessary to remove lymph nodes of patients for whom it has been determined that cancer has not metastasized to the sentinel lymph node, and the burden on such patients is thereby reduced. Moreover, this type of surgery is not limited to breast cancer, but can be employed in conjunction with open gastrointestinal tract surgery or surgical procedures utilizing a laparoscope.

One conventional method of detecting the lymph node is the colorant method, employing a blue colorant. According to this method, a blue colorant is locally injected, endermically or by use of an endoscope, into the vicinity surrounding the diseased area directly preceding the performance of cancer removal surgery; the sentinel lymph node dyed by the blue colorant is visually detected. Another known method is the RI method, wherein a radioisotope is employed as a tracer.

According to the RI method, a radioisotope is locally injected, endermically or by use of an endoscope, on the day prior to surgery into the vicinity surrounding the diseased area. The injected radioisotope advances from the position at which it was injected towards the lymph nodes and stays for a set duration at the sentinel lymph node. A few hours after the radioisotope is injected a lymphosynthography is performed, and the approximate position is marked. When the surgery to remove the cancer is performed, the marked position is cut open, and employing a gamma-probe, the gamma radiation emitted by the lymph nodes in the vicinity of the opened position is detected; the lymph node emitting the most gamma radiation is detected as the sentinel lymph node.

Further, in recent years fluorescent colorant methods employing fluorescent colorants have been proposed for detecting diseased tissue: For example, an embodiment of a sentinel lymph node detection apparatus has been disclosed in Japanese Patent Application No. 2000-124600, by the inventors of the present invention, wherein a cyanine colorant is administered to a living tissue, and by irradiation thereof by an excitation light, the diseased tissue is detected.

However, according to aforementioned conventional sentinel lymph node navigational surgery, when a determination is to be made as to whether or not cancer has metastasized to the sentinel lymph node, an on-the-spot diagnosis of the cause of the disease is performed by surgically removing the sentinel lymph node, preparing a sample thereof and examining an image of the cells contained in said sample. However, as per the case in which the early detection of breast cancer is performed as described above, for example, because the rate of metastasis of the disease to lymph nodes is 20 percent, for the 80 percent of the patients in whom the disease has not metastasized to the lymph nodes, the removal of the sentinel lymph node is unnecessary. Although there is a strong demand, accompanying the trend in recent years to preserve the QOL of the patient, for a sentinel lymph node detection method in which it is not necessary to surgically remove the sentinel lymph node, the conventional sentinel lymph node detection method and apparatus described above only disclose methods of lymph node detection, and there is no mention therein of a method or apparatus in wherein the test for pathology is performed in a manner in which the sentinel lymph node is not surgically removed.

SUMMARY OF THE INVENTION

The present invention has been developed in consideration of the circumstances described above, and it is a primary objective of the present invention to provide a sentinel lymph node optical tomographic image obtaining method and apparatus for obtaining an image of the cells of the sentinel lymph node for use in performing a test for pathology.

The method of obtaining an optical tomographic image of a sentinel lymph node according to the present invention comprises the steps of detecting the sentinel lymph node residing in the vicinity of a diseased tissue (hereinafter referred to as a target subject), scanning the detected sentinel lymph node with a signal-light having a coherence length of 5 um or less, and obtaining an ultra high resolution optical tomographic image of the sentinel lymph node by using the reflected-light reflected from a predetermined depth of said sentinel lymph node and the interference caused by the signal-light and a reference-light of a frequency slightly different from that of the signal-light.

Further, the method of detecting the sentinel lymph node can be based on a fluorescent-light image obtained of the fluorescent light, which is close to the near-infrared wavelength band, emitted from near-infrared fluorescent colorant that has been injected into an examination area of the target subject in the vicinity of the diseased portion, which includes the sentinel lymph node, upon the irradiation thereof by an excitation light having a wavelength within the wavelength range causing excitation of the near-infrared fluorescent colorant, however, it is not limited thereto; a colorant method employing a blue colorant, etc., or an RI method employing a radio isotope as a tracer can also be employed.

Here, the referents of the expression "based on a fluorescent-light image obtained of the fluorescent light, which is close to the near-infrared wavelength band" include a method, for example, wherein the intensity of the fluorescent light of each pixel constituting a fluorescent-light image formed of fluorescent light of a wavelength near the near-infrared wavelength range is compared to every other pixel constituting said fluorescent-light image, and the pixel detected as having the highest intensity is recognized as representing the sentinel lymph node, a method wherein a fluorescent-light image is converted to a visible image representing the intensity of the fluorescent light as a gradient, and detecting the sentinel lymph node by visually examining said image, etc.

Further, the scanning-position to be scanned by the signal-light can be matched the position of the sentinel lymph node detected based on the fluorescent-light image. Here, the referents of the expression "the scanning-position to be scanned by the signal-light can be matched the position of the sentinel lymph node detected based on the fluorescent-light image" include any method wherein the scanning-position to be scanned by the signal-light is determined without having to perform a manual operation therefor, and is automatically matched to the position of the sentinel lymph node detected based on the fluorescent-light image: For example, a method comprising the steps of converting a fluorescent-light image is to a visible image and then displaying said visible image on a monitor, confirming the position of the sentinel lymph node by viewing the image displayed on the monitor, inputting the position of the pixel corresponding to the position of the sentinel lymph node, and setting as the scanning-position to be scanned by the signal-light the position of the target subject that matches the position of the pixel detected as representing the sentinel lymph node, a method comprising the steps of obtaining the pixel having the highest intensity value by performing an image processing operation, and setting as the scanning-position to be scanned by the signal-light the position of the target subject that matches the position of the pixel detected as representing the sentinel lymph node, etc.

The sentinel lymph node optical tomographic image obtaining apparatus according to the present invention comprises: a sentinel lymph node detecting means; and an OCT means for scanning the detected sentinel lymph node with a signal-light, which is a low-coherence light having a coherence length of 5 um or less, and obtaining an ultra high resolution optical tomographic image of the sentinel lymph node, using the reflected-light reflected from a predetermined depth of the sentinel upon the irradiation thereof by the signal-light, and the interference caused between the signal-light and a reference-light which has a slight difference in frequency from that of the signal-light. OCT stands for Optical Coherence Tomography, which is defined as the obtaining of an optical tomographic image by using the interference caused by a low-coherence light. For a detailed explanation of OCT, refer to an article in "O Plus E" Vol.21, No. 7, pp. 802–04, by Masamitsu Haruna.

Further, an OCT means employing an optical fiber light source for emitting low-coherence light has been disclosed in Japanese Patent Application 2000-67264 filed by the inventors of the present invention. According to said OCT apparatus: the low-coherence light emitted from aforementioned light source is separated into a signal-light and a reference-light; the wavelength of the signal-light or the reference-light is slightly shifted by use of a Piezo element or the like; the target subject is irradiated with the signal-light and interference is caused between the reflected-light reflected from said target subject at a predetermined depth and the reference-light; the signal strength of the light-beat produced due to said interference is measured by a heterodyne wave detection; and the tomographic data based on the reflectance ratio of the signal-light is obtained; wherein, by very slightly moving a movable mirror, etc., disposed above the optical path of the reference-light, causing the length of the optical path of the reference-light to change slightly, and the data for a target subject can be obtained for a depth at where the length of the optical path of the reference-light and the length of the optical path of the signal-light can be made to be equal. Further, by shifting in intervals of a microscopic distance the position of the target subject to be irradiated by the signal-light, and taking a measurement at each position shifted to, that is, by scanning the target subject with the signal-light, an optical tomographic image of the scanned position can be obtained.

The sentinel lymph node detecting means comprises: an excitation light emitting means for projecting an excitation light, which has a wavelength within the wavelength range causing excitation of a near-infrared fluorescent colorant that emits fluorescent light having a wavelength band near the near-infrared wavelength band, onto the target subject including the sentinel lymph node and into the vicinity of which the near-infrared fluorescent colorant has been injected in advance, an image obtaining means for obtaining an image formed of the near-infrared fluorescent light having emitted from the target subject, and a sentinel lymph node detecting means for detecting the sentinel lymph node based on the fluorescent-light image obtained by the image obtaining means.

Here, the referent of the expression "a sentinel lymph node detecting means for detecting the sentinel lymph node based on thefluorescent-lightimageobtainedbytheimageobtainingmeans" can be, for example, a means for comparing, by use of image processing, the intensity of each pixel of a fluorescent-light image obtained by the image obtaining means and recognizing the pixel detected as having the highest intensity as the pixel representing the sentinel lymph node.

Further, the OCT means can be provided with a scanning-position control means for matching the scanning-position to be scanned by the signal-light to the position of the sentinel lymph node detected, based on the fluorescent-light image, by the sentinel lymph node detecting means.

Here, the referent of the expression "a scanning-position control means for matching the scanning-position to be scanned by the signal-light to the position of the sentinel lymph node detected, based on the fluorescent-light image, by the sentinel lymph node detecting means" can be any means which automatically, that is, requiring no manual operation to determine the scanning-position to be scanned by the signal-light, matches the position to be scanned by the signal-light to the position of the sentinel lymph node detected based on the fluorescent-light image: for example, a means for matching the scanning-position to be scanned by the signal-light to the position of the target subject corresponding to the position of the pixel within a fluorescent-light image detected as having the highest intensity, which is the pixel representing the sentinel lymph node.

It is preferable that the low-coherence light is of a wavelength within the wavelength range of 600–1700 nm.

Note that according to the present invention, the light source for emitting the low-coherence light is not limited to any specific light source; any light source that emits a low-coherence light having a coherence length of 5 um or less can be employed.

According to the method and apparatus for obtaining a sentinel lymph node optical tomographic image according to the present invention: a detected sentinel lymph node is scanned with a signal-light, which is a low-coherence light having a coherence length of 5 um or less; and an ultra high-resolution optical tomographic image of the sentinel lymph node is obtained. Because an ultra high-resolution optical tomographic image of the sentinel lymph node can be obtained by scanning the sentinel lymph node with the signal-light, it is not necessary to surgically remove the sentinel lymph node. Further, although the resolution of the ultra high-resolution optical tomographic image of the sentinel lymph node is dependent upon the coherence length of the low-coherence light, by using a low-coherence light having a coherence length of 5 um or less, the resolution of the ultra high-resolution optical tomographic image can be improved to the cellular level. Accordingly, by application of the method and apparatus for obtaining a sentinel lymph node optical tomographic image according to the present invention, an ultra high-resolution optical tomographic image of the sentinel lymph node, which attains resolution to the cellular level, can be obtained without the surgical removal thereof. If a test for pathology is carried out, by a pathologist or a pathology diagnostic apparatus, employing the ultra high-resolution optical tomographic image of the sentinel lymph node, for cases in which it is determined that the disease has not metastasized to the sentinel lymph node, that is, for cases in which it is not necessary to surgically remove the sentinel lymph node, the surgery can be completed without surgically removing the sentinel lymph node.

Further, for cases in which the detecting of the sentinel lymph node is carried out based on a near-infrared fluorescent-light image obtained of the fluorescent light having a wavelength near the near-infrared wavelength band emitted from a target subject, into the vicinity of which a near-infrared fluorescent colorant has been injected in advance into a target subject that includes the sentinel lymph node, upon the irradiation thereof by an excitation light having a wavelength near the wavelength range of light that causes excitation of a near-infrared fluorescent colorant, the target area including the sentinel lymph node can be rendered as an image, and the detection of the sentinel lymph node can be performed easily and efficiently.

Still further, when the sentinel lymph node is detected based on the aforementioned fluorescent-light image, because the position of the sentinel lymph node can be specified as the position of the pixel representative thereof occurring in the fluorescent-light image, the position within the target subject that corresponds to the position of said pixel can be automatically matched to the scanning-position to be scanned by the signal-light; whereby the necessity to perform a troublesome manual operation therefor is eliminated, an ultra high-resolution optical tomographic image can be obtained expediently and the overall benefit to patient and operator obtained by application of the present invention is improved.

Additionally, if the low-coherence light has a wavelength in the 600–1700 nm wavelength range, the signal-light exhibits desirable transmittance and dispersion characteristics with respect to the body of a patient, a desired optical tomographic image data can be obtained.

DESCRIPTION OF THE PREFERRED EMBODIMENTS

Figure 1:
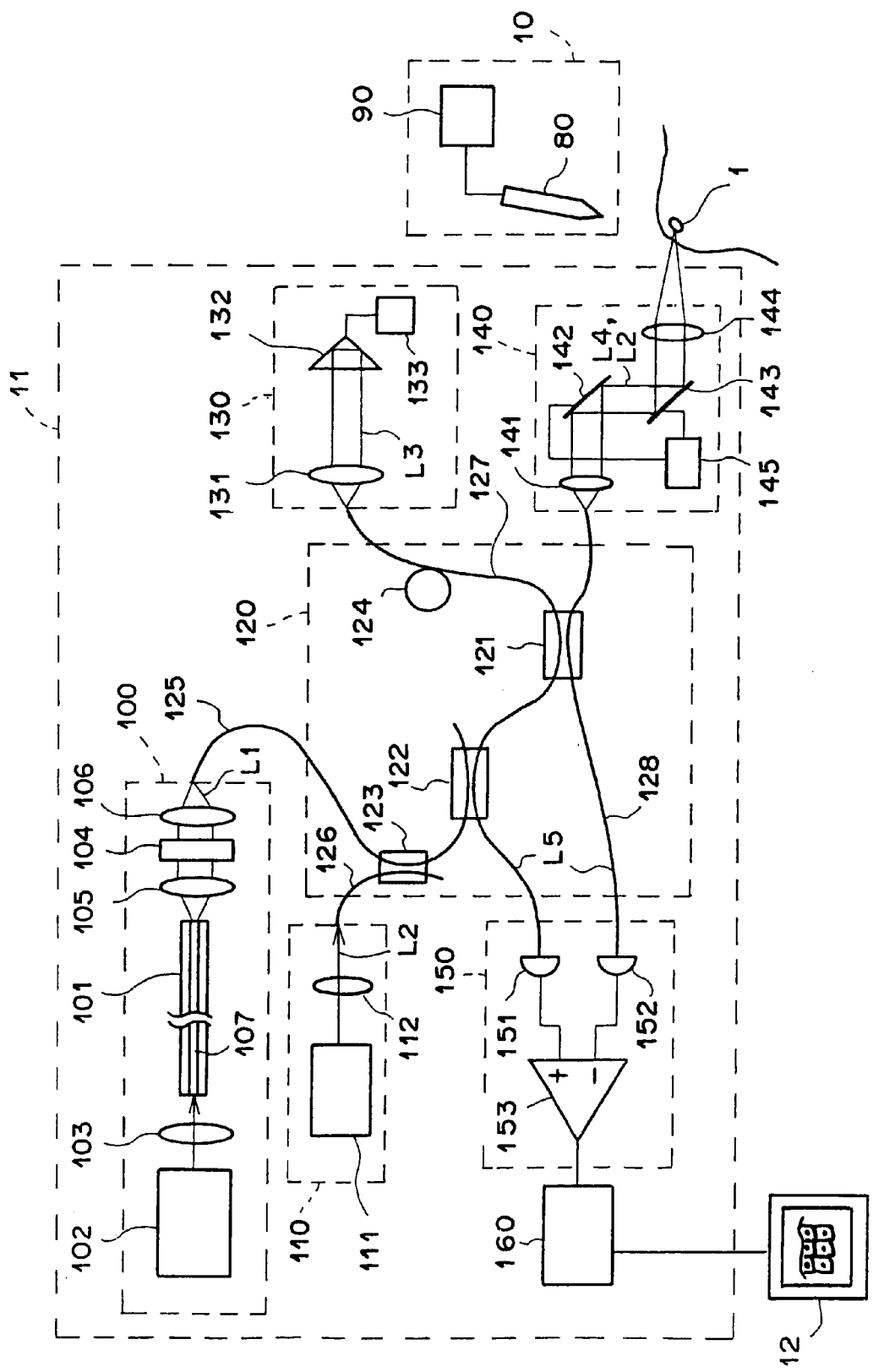
FIG. 1 is a schematic drawing of the first embodiment of a sentinel lymph node optical tomographic image obtaining apparatus according to the present invention.

Hereinafter, the preferred embodiments of the present invention will be explained with reference to the attached drawings. FIG. 1 is a schematic drawing of the first embodiment of a sentinel lymph node optical tomographic image obtaining apparatus according to the present invention in its entirety. This sentinel lymph node optical tomographic image obtaining apparatus carries out the detection of a sentinel lymph node by use of an RI method employing a radioisotope as a tracer, and obtains an ultrahigh-resolution optical tomographic image, which is a cellular level image, without the removal of the sentinel lymph node, and is applicable to open surgery.

The sentinel lymph node optical tomographic image obtaining apparatus according to the current embodiment comprises: a sentinel lymph node detecting portion 10 for detecting the sentinel lymph node by measuring the quantity of gamma radiation emitted from a radioisotope that has been injected in advance into the vicinity of a target subject including the sentinel lymph node; an OCT portion 11 for obtaining the optical tomographic data of the sentinel lymph node detected by said sentinel lymph node detecting portion 10; and a monitor 12 for displaying as a visible image the optical tomographic data obtained by the OCT means 11.

The sentinel lymph node detecting portion 10 comprises a gamma-probe 80 for measuring the quantity of gamma radiation, and a gamma radiation quantity display portion 90 for displaying the measured value obtained by the gamma-probe 80.

The OCT portion 11 comprises: a low-coherence light source 100 for emitting a low-coherence light L1 having a core wavelength of 800 nm and a coherence length of 1.4 um; an aiming light source 110 for emitting an aiming light L2, which is visible light; a fiber optics coupling system 120 for combining the low-coherence light L1 and the aiming light L2, and for separating and combining the reference-light L3 and signal-light L4 of the low-coherence light L1; an optical path extending portion 130 disposed along the optical path of the reference-light L3, which causes the length of the optical path of said reference-light L3 to change; a light scanning portion 140 for scanning a sentinel lymph node 1 with the signal-light L4; a balance differential detecting portion 150 for detecting the signal strength of the interference light L5 between the signal-light L4' reflected from a predetermined surface of the sentinel lymph node 1 and the reference-light L3; and a signal processing portion 160 for performing a heterodyne detection process to obtain the strength of the signal-light L4' reflected from a predetermined surface of the sentinel lymph node 1 from the strength of the interference light L5 detected by the balance differential detection portion 150, and forming optical tomographic image data.

The light source portion 100 of the OCT portion 11 is provided with an optical fiber light source 101 for emitting low-coherence light upon the entry therein of an excitation light; a semiconductor laser 102 for emitting a laser beam having a wavelength of 660 nm, which serves as the excitation light used to excite said optical fiber light source 101; a lens 103 for focusing the excitation light onto the input face of the optical fiber light source 101; an excitation light cutoff filter 104 for cutting off light having a wavelength of 700 nm or shorter, which includes the excitation light, from the low-coherence light; and a lens 105 and a lens 106 for focusing the low-coherence light emitted from the optical fiber light source 101.

The optical fiber light source is an optical fiber having a core 107 at the center thereof, and said core 107 has been doped with colorants that absorb excitation light and emit light. When the excitation light enters the fiber 101, a low-coherence light having a core wavelength of substantially 800 nm and a coherence length of 1.4 um is emitted from the output face thereof.

The aiming-light source portion 110 comprises a semiconductor laser 111 for emitting a red laser beam that serves as the aiming-light L2, and a lens 112 for focusing the aiming-light L2 emitted from said semiconductor laser 111.

The fiber optics coupling system 120 comprises: a fiber coupler 121 for separating the low-coherence light emitted from the optical fiber light source 101 into a signal-light L4 and a reference-light L3, and for combining the signal-light L4' reflected from a predetermined depth of the sentinel lymph node 1 and the reference-light L3 to obtain an interference light L5; a fiber coupler 122 and a fiber coupler 123 provided between the light source portion 100 and the fiber coupler 121; a Piezo element 124 for slightly shifting the frequency of the reference-light L3; a fiber 125 for connecting the light source portion 100 and the fiber coupler 122; a fiber 126 for connecting the aiming-light source portion 110 and the fiber coupler 123; a fiber 127 for connecting the balance differential detecting portion 150 and the optical path extending portion 130, by way of the fiber couplers 121 and 122; and a fiber 128 for connecting the light-scanning portion 140 and the balance differential detecting portion 150, by way of the fiber coupler 121. Note that the fibers 125, 127, and 128 are single mode optical fibers.

The optical path extension portion 130 comprises: a lens 131 for converting the reference-light L3 emitted from the fiber 127 to a parallel light and for causing the reflected reference-light L3 to enter the fiber 127; a prism 132 for changing the length of the optical path of the reference-light L3 by moving said prism in the horizontal direction indicated in FIG. 1; and a drive unit 133 for moving said prism 132 in the horizontal direction.

The light scanning unit 140 comprises: a lens 141 for guiding the signal-light L4 emitted from the fiber 128 to the sentinel lymph node 1, and for causing the reflected signal-light L4' to enter the fiber 128; a mirror 142; a mirror 143; a lens 144; and a drive portion 145 for driving the mirrors 142 and 143. The drive portion 145 is connected to a manual input portion (not shown), and depending on a manual input to said manual input portion, a desired straight line portion is scanned by the light scanning portion 140. Note that the light scanning portion 140 is a part of an attachment for use in open surgery (not shown).

The balance differential detecting portion 150 comprises a photodetector 151 and a photodetector 152 for measuring the signal strength of the interference light L5, and a differential amplifier 153 for adjusting the input balance of the detection values output by the photodetectors 151 and 152 and canceling out the noise component and drift component thereof, and then amplifying the difference therebetween.

Next, the operation of the sentinel lymph node optical tomographic image obtaining apparatus according to the first embodiment will be explained. First, a radioisotope is locally injected, endermically or by use of an endoscope, on the day prior to surgery into the vicinity of the target subject. The injected radioisotope advances towards the lymph nodes from the injection position, and stays for a set duration at the sentinel lymph node. A few hours after the radioisotope is injected a lymphosynthography is performed, and the approximate position is marked. When the surgery to remove the cancer is performed, the marked position is cut open, and the quantity of gamma radiation emitted by the lymph nodes in the vicinity of the opened position is measured by the gamma-probe 80 as the position of the gamma-probe 80 is shifted in intervals of a microscopic distance. The operator, based on the measured value displayed on the gamma radiation quantity display portion 90, detects as the sentinel lymph node the lymph node emitting the most gamma radiation.

After the sentinel lymph node has been detected, an optical tomographic image thereof is obtained; at this time, it is not necessary to surgically remove the sentinel lymph node from the body of the patient.

When an optical tomographic image is to be obtained, first, the red aiming-light L2 emitted from the semiconductor laser 111 of the aiming-light source portion 110 is focused by the lens 112 and enters the fiber 126. The aiming-light L2 passes through the fiber 126, the fiber coupler 123, the fiber 125, the fiber coupler 122, the fiber 127, the fiber coupler 121, and the fiber 128, and is projected onto the sentinel lymph node 1 as a red spot beam by way of the lens 141, the mirror 142, the mirror 143 and the lens 144.

The angle at which the mirror 142 and the mirror 143 are disposed is controlled by the drive portion 145, in response to a manual input inputted to a manual input portion (not shown) The operator sets the measurement starting position and the measurement finishing position at the drive portion 145, by use of the aiming-light, after the operator has controlled the angle of the mirrors 142 and 143 so that the aiming light L2 is projected onto the sentinel lymph node 1.

After the position of the measurement area has been set, the low-coherence light for obtaining an optical tomographic image is emitted from the light source portion 100. When the measurement operation is initiated, the mirrors 142 and 143 are controlled by the drive portion 145 so as to be disposed at the angle at which the measurement initiation position is irradiated by said low-coherence light.

First, the excitation light having a wavelength of 600 nm emitted from the semiconductor laser 102 is focused by the lens 103 and enters the core 107 of the optical fiber light source 101. As the excitation light is conveyed within the core 107, said excitation light is absorbed by the colorant with which the core 107 has been doped. The colorant absorbing the excitation light makes the transition from the base state to the excitation state; the colorant returns to the base state from the excitation state through the thermal relaxation and light emission processes. Because the optical fiber light source 101 is not structured as an optical resonator, each individual light emitted is randomly amplified, with no interrelatedness therebetween; the light is conveyed through the core 107, and emitted from the output face of the optical fiber light source 101 as spontaneously emitted light.

This spontaneously emitted light is a low-coherence light L1 having the spectral characteristics determined by the spectra produced by the colorant with which the core 107 has been doped, and the conveyance characteristics of the optical fiber light source 101. Further, the intensity of the low-coherence light L1 is dependent upon the quantity of colorant with which the core 107 has been doped. That is to say, by selecting an appropriate type and quantity of colorant with which the core fiber is to be doped, as well as an appropriate length for the fiber optical light source 101, a low-coherence light L1 having a desired core wavelength, spectral width and intensity can be obtained.

The optical fiber light source 101 employed in the current embodiment emits low coherence light L1 having a core wavelength of substantially 800 nm and a coherence length of 1.4 um; said low coherence light L1 is converted to a parallel light by the lens 105, and after being transmitted by the excitation light cutoff filter 104, is focused by the lens 106 and enters the fiber 125.

The low coherence light which passed through the fiber 125 enters the fiber 127 at the fiber coupler 122, and is separated at the fiber coupler 121 into a reference-light L3 that proceeds within fiber 127 in the direction toward the optical path extending portion 130, and a signal-light L4 that proceeds within the fiber 128 in the direction toward the light scanning portion 140.

The reference-light L3 is modulated by the Piezo element 124 provided along the optical path, causing a slight difference Δf between the frequency of the reference-light L3 and the frequency of the signal-light L4 to occur.

The signal-light L4 is projected onto the sentinel lymph node 1 by way of the lens 141, mirror 142, mirror 143, and lens 144 of the light scanning unit 140. The signal-light L4', which is the component of the signal-light L4 entering the sentinel lymph node 1 that has been reflected at a predetermined depth thereof, is fed back via the lens 141, the mirror 142, the mirror 143, and the lens 144 to the fiber 128. The signal-light Ls' that is fed back to the fiber 128 is combined in the fiber 121 with the reference-light L3 fed back to the fiber 127, which is described below.

On the other hand, the reference-light L3 that has been modulated by the Piezo element 124 passes through the fiber 127 and enters the prism 132 through the lens 131 of the optical path extending portion 130, said modulated reference-light L3 is then reflected by the prism 132 and is again transmitted by the lens 131 and fed back to the fiber 127. The reference-light L3 fed back to the fiber 127 is combined in the fiber 121 with the signal-light L4' described above.

The signal-light L4' and the reference-light L3 combined in the fiber 121 are again combined along the same axis, and at a predetermined timing, interference is caused between said signal-light L4' and reference-light L3, whereby said signal-light L4' and reference-light L3 become an interference light L5 and a beat signal is produced.

Because the signal-light L4' and the reference-light L3 are low-coherence light of a short interference-susceptibility distance, after the low-coherence light has been separated into the signal-light L4 and the reference-light L3, if the length of the optical path of the signal-light L4 (L4') up to the point at which said signal-light L4 (L4') arrives at the fiber 121 is substantially the same as the length of the optical path of the reference-light L3 up to the point at which said reference-light L3 arrives at the fiber 121, both of said lights interfere with each other, said interference repeats in a strong-weak cycle according to the difference Δf between the frequencies of the reference-light L3 and the signal-light L4, and a beat signal is generated thereby.

The interference light L5 is separated in the fiber coupler 121: one of the separated components thereof enters the photodetector 151 of the balance differential detector 150 after passing through the fiber 127; and the other of the separated components thereof enters the photodetector 152 after passing through the fiber 128.

The photodetectors 151 and 152 detect the signal strength of the beat signal from the interference light L5, and the differential amplifier 153 obtains the difference between the detection value of the photodetector 151 and the detection value of the photodetector 152 and outputs said difference to the signal processing portion 160. Note that because the differential amplifier 153 is provided with a function for adjusting the balance of the direct current component of the value input thereto, even in a case, for example, in which drift occurs in the low-coherence light emitted from the light source portion 100, by amplifying the difference after adjusting the balance of the direct current component, the drift component is cancelled out, and only the beat signal component is detected.

Note that here, the prism 132 is aligned, by the drive portion 133, along the direction of the light axis. Therefore, the length of the optical path of the reference-light L3 up to the point at which said reference-light L3 arrives at the fiber 121 changes. Because the length of the optical path of the reference-light L3 and the signal-light L4 (L4') that interferes therewith is changed thereby, the depth at which the tomographic data of the sentinel lymph node 1 is obtained also changes.

According to the operation described above, after the tomographic data of a predetermined point on a sentinel lymph node 1 at a desired depth from the surface has been obtained, the entry point of the signal-light L4 is moved by the slight movement of the mirror 142 and the mirror 143 of the light scanning portion 140 in the direction of the finishing position of the measurement operation, which has been set in advance at the drive portion 145, and the tomographic data is obtained to a predetermined depth in the same way. By repeating the above-described operation, the optical tomographic data of the target subject 10 can be obtained from the starting position of the measurement operation to the finishing position thereof.

The signal processing portion 160 performs a heterodyne detection to detect the strength of the signal-light L4' reflected by a predetermined surface of the sentinel lymph node 1 from the signal strength of the interference light L5 detected by the balance differentiation detecting portion 150, converts the obtained strength of the signal-light L4' to optical tomographic data, and outputs said optical tomographic data to the monitor 12.

The monitor 12 displays as a visible-image the optical tomographic image data output from the image processing portion 160. Note that by utilizing the low-coherence light having a coherence length of 1.4 μm emitted from the light source portion 100, it becomes possible to obtain an ultra high resolution optical tomographic image, the resolution of which is improved to the cellular level.

According to the operation described above, an ultra high resolution optical tomographic images, which is a cellular image, of the sentinel lymph node 1 can be obtained without surgically removing the sentinel lymph node 1. Therefore, if a test for pathology is carried out, by a pathologist or a pathology diagnostic apparatus, employing this ultra high-resolution optical tomographic image of the sentinel lymph node, for cases in which it is determined that the disease has not metastasized to the sentinel lymph node, that is, for cases in which it is not necessary to surgically remove the sentinel lymph node, the surgery can be completed without surgically removing the sentinel lymph node. Further, because the wavelength of low-coherence light is 800 nm, the signal-light exhibits desirable transmittance and dispersion characteristics with respect to the sentinel lymph node 1, and a desired optical tomographic image data can be obtained.

Figure 2:
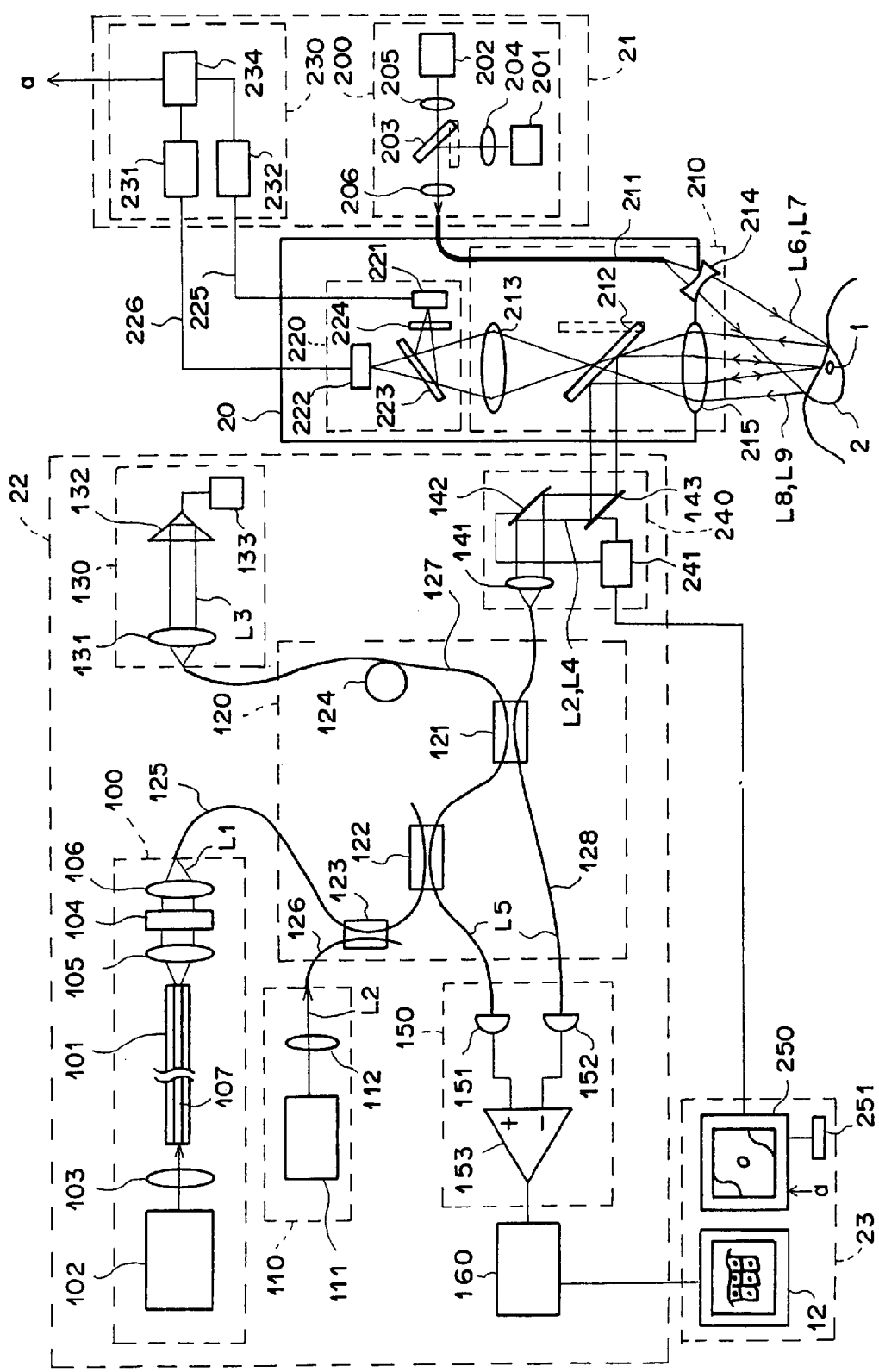
FIG. 2 is a schematic drawing of the second embodiment of a sentinel lymph node optical tomographic image obtaining apparatus according to the present invention.

Next, the second embodiment of a sentinel lymph node optical tomographic image obtaining apparatus implementing the sentinel lymph node optical tomographic image obtaining method according to the present invention will be explained with reference to FIG. 2. FIG. 2 is a schematic drawing of the second embodiment of a sentinel lymph node optical tomographic image obtaining apparatus according to the present invention in its entirety.

This apparatus is implemented in the form of a laparoscope, and operates as follows: the cyanine colorant indocyanine green is injected into the body of the patient in the vicinity of the target subject; the target subject is then irradiated with an excitation light having a wavelength near the near-infrared wavelength band; a near-infrared fluorescent-light image formed of the near-infrared fluorescent light emitted from the target subject upon the irradiation thereof by the excitation light is obtained; said obtained near-infrared fluorescent-light image is converted to a visible-image and displayed; the sentinel lymph node which has emitted the fluorescent light is detected; and an optical tomographic image of the detected sentinel lymph node is obtained.

The sentinel lymph node optical tomographic image obtaining apparatus according to the current embodiment comprises: a laparoscope 20 to be inserted into the body of a patient; a target-subject image obtaining means 21 for obtaining a reflectance image and a near-infrared fluorescent-light image of the target subject; an OCT portion 22 for obtaining an optical tomographic image of the target subject; and a display portion 23 for displaying a target-subject image formed of the superimposed reflectance image and near-infrared fluorescent-light image, and the optical tomographic image of the sentinel lymph node. Note that elements common to the first embodiment shown in FIG. 1 are likewise labeled, and in so far as it is not particularly required, further explanation thereof has been omitted.

The laparoscope 20 is provided with an insertion portion 210, and an image obtaining portion 220. The insertion portion 210 comprises: a light guide 211 extending internally to the distal end thereof; a switching mirror 212 for reflecting, when said mirror 212 is disposed in the position indicated by the solid line, the signal-light L4 and the aiming light L2; and a lens 213 for focusing a reflectance image formed of the reflected-light L8 of the white-light L6, and a near-infrared fluorescent-light image formed of the near-infrared fluorescent light L9. Further, an illuminating lens 214 and an objective lens 215 are provided at the distal end of the light guide 211 and the switching mirror 212, that is, at the distal end of the insertion portion 210. The light guide is formed of a composite glass fiber, and is connected to the illuminating unit 200, which is described below.

The image obtaining portion 220 is provided with: a near-infrared CCD 221 for obtaining a near-infrared fluorescent-light image; a color CCD 222 for obtaining a reflectance image; a dichroic mirror 223 for separating the near-infrared fluorescent light L9 and the reflected-light L8; an excitation light cutoff filter 224 for cutting the reflected excitation light L7 from the reflected light L8, which has both said excitation light L7 and the near-infrared fluorescent light L9 as its components; a CCD cable 225, which is connected to the near-infrared CCD 221, for conveying an obtained image signal; and a CCD cable 226, which is connected to the color CCD 222, for conveying an obtained image signal. Note that the dichroic mirror 223 transmits light having a wavelength of 780 nm or shorter and reflects light having a wavelength longer than 780 nm, and the excitation light cutoff filter 224 cuts light having a wavelength of 800 nm or shorter.

The target-subject image obtaining portion 21 comprises an illumination unit 200 provided with a light source that emits white-light for obtaining a reflectance image and excitation light for obtaining a fluorescent-light image, and an image processing portion 230. The illumination unit 200 comprises: a semiconductor laser 201 that emits an excitation light L7 having a wavelength of 790 nm; a white-light source 202 for emitting a white-light L6 for obtaining a reflectance image; and a switching mirror 203 that switches between the irradiating of the white-light L6 and the excitation light L7 according to a predetermined timing.

The image processing unit 230 comprises: a reflectance image forming portion 231 for performing the image processing to display a reflectance image as a color image; a fluorescent-light image forming portion 232 for performing the image processing to display a near-infrared fluorescent-light image as a gradation image; and a superimposed-image forming portion 234 for superimposing the color image of a reflectance image and the gradation image of a near-infrared fluorescent-light image.

The reflectance image forming portion 231 performs image processing on a reflectance image obtained by the color CCD 222 to form a color image signal, and after being digitized, said color image signal is temporarily stored in a memory (not shown) The color image signal is read out from the memory in synchronization with the display timing, and after being D/A converted, said color image is again converted to a video signal and output to the superimposed-image forming portion 234.

The fluorescent-light image forming portion 232 performs image processing on a reflectance image obtained by the near-infrared CCD 221 to form a gradation image signal, and after being digitized, said gradation image signal is temporarily stored in a memory (not shown). The gradation image signal is read out from the memory in synchronization with the display timing, and after being D/A converted, said gradation image is converted again to a video signal and output to the superimposed-image forming portion 234.

The superimposed-image forming portion 234 superimposes the color image signal output from the reflectance image forming portion 231 and the gradation image signal output from the fluorescent-light image forming portion 232, and outputs said superimposed color image signal and gradation image signal as a display image signal to the monitor 250 of the display portion 23, which is described below.

The OCT portion 22 is provided with: a light source portion 100 for emitting a low-coherence light L1; an aiming light source portion 110 for emitting an aiming light L2; a fiber optics coupling system 120 for performing the separating and combining of each light; an optical path extending portion 130 for changing the length of the optical path of the reference-light L3; a light scanning portion 240 for scanning the sentinel lymph node 1 of the target subject with the signal-light L4; a balance differential detecting portion 150 for detecting the signal strength of the interference light L5; and a signal processing portion 160 for performing a heterodyne detection and forming optical tomographic image data.

The light scanning portion 240 is provided with a lens 141 for guiding the signal-light L4 emitted from the fiber 128 to the insertion portion 210 and also for causing the signal-light L4' reflected from the sentinel lymph node 1 to enter the fiber 128; a mirror 142 and a mirror 143; and a control portion 241 for controlling the angle at which the mirror 142 and the mirror 143 are disposed. The control portion 241 is connected to the monitor 250, which is described below, and controls the angle at which the mirror 142 and he mirror 143 are disposed so that the specified pixel position of the target-subject image displayed on the monitor 250 matches the scanning-position to be scanned by the signal-light L4.

The display portion 23 is provided with a monitor 12 for displaying an optical tomographic image, a monitor 250 for displaying a target-subject image; and a pen-type input portion for specifying a desired pixel position on the target-subject image displayed on the monitor 250. Note that each part is connected to a controller (not shown), and the operation timing thereof is controlled thereby.

Hereinafter, the operation of the sentinel lymph node optical tomographic image obtaining means of the configuration described above will be explained. First, the operation occurring when a target-subject image is obtained and the sentinel lymph node for a tumor occurring in the digestive tract of a patient is to be detected will be explained; then, the operation occurring when an optical tomographic image of the sentinel lymph node is to be obtained will be explained.

Figure 3:
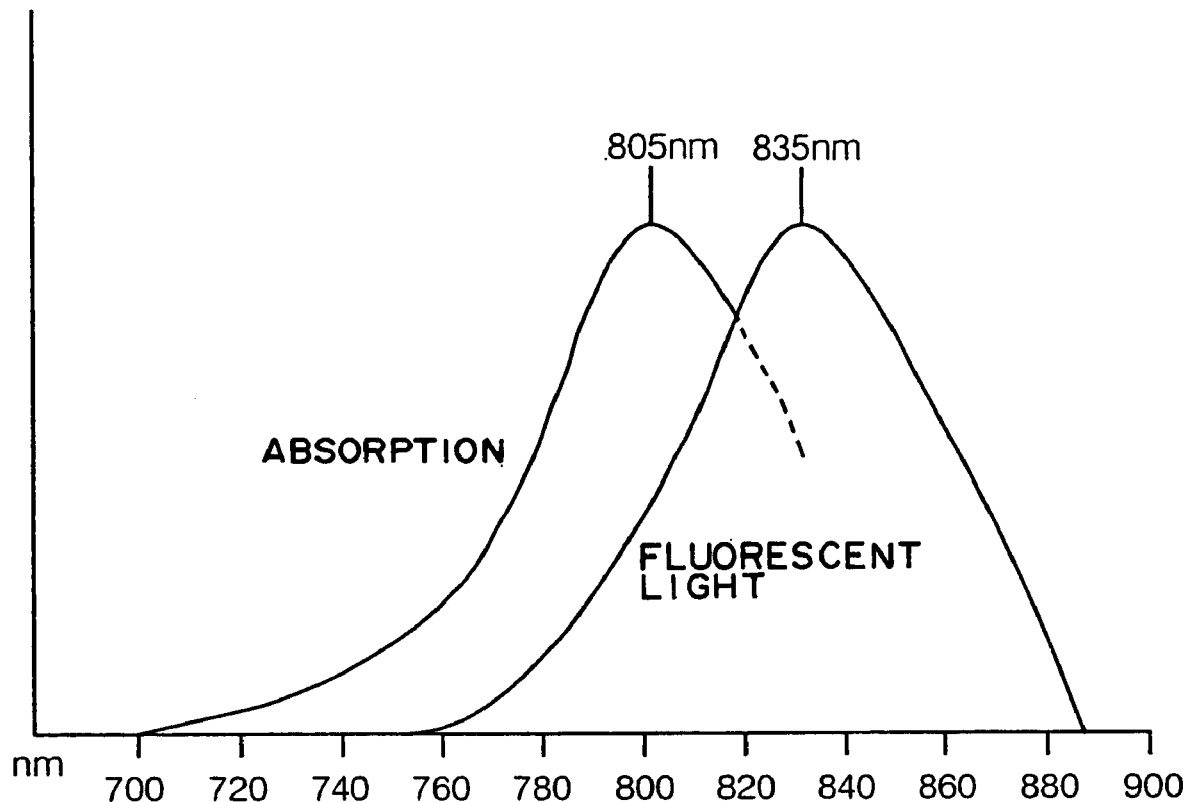
FIG. 3 is graph showing the spectra of light absorbed by indocyanine green, and the fluorescent spectra.

At a predetermined time before surgery employing a laparoscope is to be performed, an endoscope is inserted into the digestive tract of the patient through the patient's mouth, and 5 mg of the cyanine type colorant indocyanine green per Kg of bodyweight of the patient is locally injected into the vicinity of a tumor. The indocyanine green binding to the proteins of blood vessels shows the fluorescent spectra and the absorption spectra as shown in FIG. 3; the longest wavelength that the indocyanine green can absorb is 805 nm, and the longest wavelength of fluorescent light is 835 nm.

After a predetermined period of time has passed and it is time to perform the surgery employing the laparoscope apparatus, the indocyanine green that has been locally injected into the vicinity of a tumor has passed through the lymph system and is accumulated on the sentinel lymph node 11. The sentinel lymph node 11 is covered by a layer of tissue, such as fat, having a thickness of 1 cm or less. The detecting of the sentinel lymph node is carried out under these circumstances.

According to the sentinel lymph node optical tomographic image obtaining means of the current embodiment, the obtaining of a reflectance image and the obtaining of a near-infrared image is performed in a time-division manner. For the sake of simplicity in explanation, first, the operation occurring when a reflectance image is to be obtained will be explained, and then the operation occurring when a fluorescent-light image is to be obtained will be explained. When either of the aforementioned two images is to be obtained, the switching mirror 212 with which the laparoscope insertion portion 210 is provided is disposed in the position indicated by the broken line so as not to interfere with the progress of the reflected-light L8 and the near-infrared fluorescent-light L9.

First, when a reflectance image is to be obtained, the switching mirror 203 within the illumination portion 200 is moved to the position indicated by the broken line so as not to interfere with the progress of the white-light L6. The white-light L6 emitted from the white-light source 202 is enters the light guide 211 via the lens 205 and the lens 206, and after being guided to the distal end of the insertion portion 210 of the laparoscope insertion portion 210, said white-light L6 is projected onto the target subject 2, which includes the sentinel lymph node 1, by the illuminating lens 214.

The reflected-light L8 of the white-light L6 is focused by the objective lens 215 and focused onto the color CCD 222 by the lens 213. The image signal obtained by photoelectrically converting the reflectance image is output to the reflectance image forming portion 231 via the CCD cable 225.

The reflectance image forming portion 231 first performs image processing such as amplification, blanking, clamping, 2-bit relative sampling, etc. on the image signal obtained by the color CCD 222, and then separates the processed image signal obtained thereby into a brightness signal and a color signal, and computes a color image signal. After this, the color image signal is digitized and stored in a memory. The color image signal read out of the memory according to a display timing is converted into an analog signal, then converted further into a video signal. Said video signal is output to superimposing image forming portion 234, and is output to the monitor 250, after being superimposed with the gradation image signal of the fluorescent image described below, as a target area image signal.

Next, the operation occurring when a fluorescent-light image is to be displayed will be explained. The switching mirror 203 is moved to the position indicated by the solid line so as not to reflect in the direction of the light guide 211 the excitation light L7 emitted from the semiconductor laser 201. The excitation light L7 emitted from the semiconductor laser 201 is directed toward the switching mirror 203 via the lens 204. The excitation light L7 reflected by the switching mirror 203 enters the light guide 211 via the lens 206, and after being guided to the distal end of the insertion portion 210 of the laparoscope insertion portion 210, said white-light L6 is projected onto the target subject 2, which includes the sentinel lymph node 1, by the illuminating lens 214.

The near-infrared fluorescent light L9 emitted from the target subject 2 and the reflected-light of the excitation light L7 are focused by the focusing lens 215 and the lens 213, reflected by the dichroic mirror 223, and enter the excitation light cutoff filter 224. The reflected-light of the excitation light L7 is cut by the excitation light cutoff filter 224, and only the near-infrared fluorescent light L9 enters the near-infrared CCD 221. The light-sensitive portion of the near-infrared CCD 221 photoelectrically converts the near-infrared fluorescent light L9, corresponding to the strength and weakness thereof, entering therein to obtain a signal charge, which is then output to the fluorescent-light image forming portion 232.

Figure 4A:
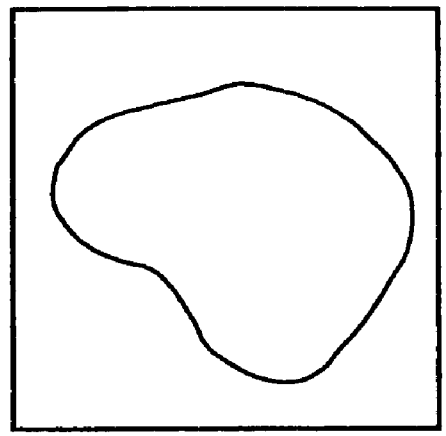
FIGS. 4A, 4B, and 4C are drawings provided for illustrating that which is displayed on the display screen.
Figure 4B:
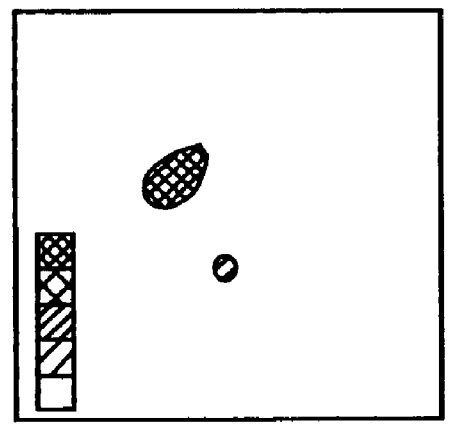
Figure 4C:
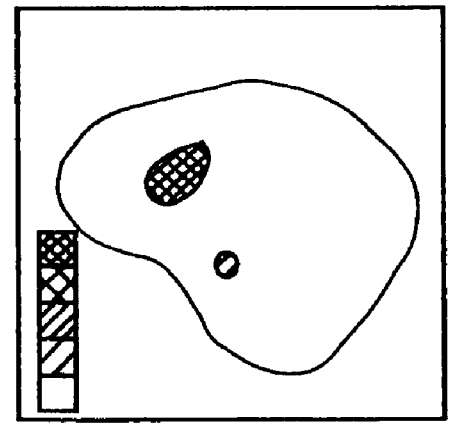

The fluorescent-light image forming portion 232 performs image processing such as amplification, blanking, clamping, 2-bit relative sampling, etc. on the image signal output by the near-infrared CCD 221, and forms, corresponding to the strength and weakness of the near-infrared fluorescent light, a gradation signal of the green color. After being digitized, said gradation signal is temporarily stored in a memory. The gradation signal is read out from the memory in synchronization with the display timing and D/A converted, and then converted to a video signal and output to the superimposed-image forming means 234; after being superimposed with the above-described color image signal, the superimposed signals are output to the monitor 250 as a target-subject image signal. If the reflectance image is a color image such as that shown in FIG. 4A, and the fluorescent-light image is a gradation image such as that shown in FIG. 4B, the image formed by superimposing the color image signal and the gradation image signal is a target-subject image such as that shown in FIG. 4C.

The monitor 250 converts the video signals input thereto to display image signals and displays said display image signals. The basic tone of the reflectance image becomes the red of the target subject, and because the higher the intensity of the light the denser the green of the gradation image becomes, the portion having the highest light intensity, that is, the place indicating the location of the sentinel lymph node 1, is displayed as yellow. Note that the operation timing of the series of operations described above is controlled by the controller.

The operator views the monitor 250 displaying the image of the target subject 2, and can discern the position of the sentinel lymph node 1 therein. For cases in which the sentinel lymph node is covered in fatty tissue or the like, after such tissue is peeled away, the measurement starting position and measurement finishing position of the operation to obtain an optical tomographic image are set from the image displayed on the monitor 250, by use of the pen-type input portion 253.

The control portion 241 of the light scanning portion 240 computes the positions on the target subject to be scanned by the signal-light L4, based on the pixel positions of the measurement starting position and the measurement finishing position input into the monitor 250, and controls the angle of the mirror 142 and the mirror 143. Then, an optical tomographic image is obtained by the same operation as occurred in the first embodiment, and is displayed on the monitor 12.

According to the operation described above, the same effect as that obtained in the first embodiment is obtained, and moreover, because the sentinel lymph node 1 is detected by visually examining a fluorescent-light image obtained of the fluorescent light having a wavelength near the near-infrared wavelength band emitted from a target subject including the sentinel lymph node, into the vicinity of which a near-infrared fluorescent colorant has been injected in advance, upon the irradiation thereof by an excitation light, which has been converted to a visible-image and displayed, the sentinel lymph node can be detected easily and efficiently.

Further, by specifying the pixel position that represents the sentinel lymph node in the target-subject image, because the scanning-position to be scanned by the signal-light L4 can be automatically controlled so as to be the position of the sentinel lymph node 1, the need to perform a cumbersome manual operation therefore is eliminated and an ultra high-resolution optical tomographic image of the sentinel lymph node 1 can be expediently obtained, whereby the overall benefit of employing the apparatus according to the current embodiment is improved.

Note that according to the current embodiment, although the measurement starting position and the measurement finishing position have been specified on the target-subject image by use of a pen-type input portion 251, the current embodiment is not limited thereto: for example, the measurement starting position and the measurement finishing position have been specified on the target-subject image by clicking on the position indicated by a cursor pointing thereto; by inputting coordinates specifying the measurement starting position and the measurement finishing position; etc.

Still further, according to the current embodiment, although the detecting of the sentinel lymph node has been performed by visually examining a target-subject image formed by superimposing a fluorescent-light image, which is a gradient image, and a color image of a reflectance image, the current embodiment is not limited thereto: for example, the sentinel lymph node can be detected by examining an image displaying the intensity of the fluorescent light as a numerical value; the sentinel lymph node can be automatically detected by subjecting the area of a fluorescent-light image having the highest intensity of near-infrared fluorescent light to image processing; etc.

In addition, according to the current embodiment, although a switching mirror 212 has been employed at the distal end of the insertion portion 210 of the laparoscope portion 20 as an optical element for reflecting the aiming light L2 and the signal-light L4, the current embodiment is not limited thereto; for example, a dichroic mirror or a half mirror can be used in place thereof. That is to say, any optical element that transmits at least one of the reflected-light L8 and the near-infrared fluorescent-light L9 and reflects at least one of the aiming light L2 and signal-light 4 can be employed.

What is claimed is:

1. A method of obtaining a sentinel lymph node optical tomographic image comprising the steps of:
   detecting a sentinel lymph node which exists in the vicinity of a target subject,
   scanning the detected sentinel lymph node with a signal-light which is a low-coherence light having a coherence length of 5 um or less, and
   obtaining an ultra high-resolution optical tomographic image of the sentinel lymph node by using the signal-light reflected from a predetermined depth of said sentinel lymph node and a reference-light having a slight difference in frequency with respect to said signal-light.

2. A method of obtaining a sentinel lymph node optical tomographic image as defined in claim 1, wherein the detecting of the sentinel lymph node comprises the steps of
   injecting in advance a near-infrared colorant that emits fluorescent light having a wavelength near the near-infrared wavelength band into the vicinity of a target subject including the sentinel lymph node, irradiating said target subject including the sentinel lymph node with an excitation light having a wavelength within the wavelength band causing excitation of said near-infrared fluorescent colorant, obtaining a fluorescent-light image formed of near-infrared fluorescent light emitted from said target subject upon the irradiation thereof by said excitation light, and detecting the sentinel lymph node based on said obtained fluorescent-light image.

3. A method of obtaining a sentinel lymph node optical tomographic image as defined in claim 2, wherein
the position of the detected sentinel lymph node is matched with the scanning-position to be scanned with the signal-light.

4. The method of claim 2, wherein the fluorescent image of the target subject is displayed by a device including a charge coupled device (CCD).

5. The method of claim 1, wherein the wavelength of the low coherence light falls between a range 600–1000 nm.

6. The method of claim 5, wherein the scanning comprises scanning the signal light along a linear path to scan the sentinel lymph node.

7. The method of claim 6, wherein the scanning of the lymph node and obtaining the image of the lymph node are performed in vivo.

8. The method of claim 1 wherein detection of the sentinel lymph node comprises injection of a radioisotope to permeate the vicinity of the target substrate.

9. An apparatus for obtaining a sentinel lymph node optical tomographic image, comprising
sentinel lymph node detecting means for detecting a sentinel lymph node which exists in the vicinity of a target subject, and an OCT means for scanning the detected sentinel lymph node with a signal-light, which is a low-coherence light having a coherence length of 5 um or less, and obtaining an ultra high-resolution optical tomographic image of the sentinel lymph node by using the reflected-light reflected from a predetermined depth of said sentinel lymph node and a reference-light having a slight difference in frequency with respect to said signal-light.

10. An apparatus for obtaining a sentinel lymph node optical tomographic image as defined in claim 9, wherein
the sentinel lymph node detecting means comprises an excitation light emitting means for projecting onto the target subject an excitation light having a wavelength within the wavelength band causing excitation in a near-infrared fluorescent colorant that emits fluorescent light having a wavelength near the near-infrared wavelength band and which has been injected in advance into the vicinity of a target subject including the sentinel lymph node, an image obtaining means for obtaining a fluorescent-light image formed of the near-infrared fluorescent light emitted from said target subject upon the irradiation thereof by said excitation light, and a detecting means for detecting, based on the fluorescent-light image obtained by said image obtaining means, the sentinel lymph node.

11. An apparatus for obtaining a sentinel lymph node optical tomographic image as defined in claim 10, wherein
the OCT means is provided with a scanning-position control means for matching the scanning-position to be scanned by the signal-light to the position of the sentinel lymph node detected, based on the fluorescent-light image, by the detecting means.

12. An apparatus for obtaining a sentinel lymph node optical tomographic image as defined in either of claims 9, 10, or 11, wherein
the wavelength of the low-coherence light falls within the 600–1700 nm wavelength range.

* * * * *